United States Patent [19]

Gerster

[11] Patent Number: 5,037,986

[45] Date of Patent: * Aug. 6, 1991

[54] OLEFINIC 1H-IMIDAZO[4,5-C]QUINOLIN-4-AMINES

[75] Inventor: John F. Gerster, Woodbury, Minn.

[73] Assignee: Minnesota Mining and Manufacturing Company, St. Paul, Minn.

[*] Notice: The portion of the term of this patent subsequent to May 29, 2007 has been disclaimed.

[21] Appl. No.: 484,871

[22] Filed: Feb. 26, 1990

Related U.S. Application Data

[63] Continuation-in-part of Ser. No. 327,693, Mar. 23, 1989, Pat. No. 4,929,624.

[51] Int. Cl.$^5$ ............................................. C07D 471/02
[52] U.S. Cl. ........................................................ 546/82
[58] Field of Search .................................... 546/82, 159

[56] References Cited

U.S. PATENT DOCUMENTS

| | | | |
|---|---|---|---|
| 4,552,874 | 11/1985 | Mardin et al. | 514/222 |
| 4,563,525 | 1/1986 | Campbell, Jr. | 546/82 |
| 4,689,338 | 8/1987 | Gerster | 514/293 |
| 4,698,346 | 10/1987 | Musser et al. | 514/293 |
| 4,698,348 | 10/1987 | Gerster | 514/293 |

OTHER PUBLICATIONS

J. Org. Chem. 15, 1278–1284 (1950) (Bachman et al.).
J. Med. Chem. 11, pp. 87–92 (1968) (Jain et al.).
Chem. Abs. 85, 94362 (1976) (Baranov et al.).
J. Heterocyclic Chem. 18, 1537–1540 (1981) (Berenyi et al.).

Primary Examiner—Catherine S. K. Scalzo
Attorney, Agent, or Firm—Gary L. Griswold; Walter N. Kirn; Douglas E. Reedich

[57] ABSTRACT

Novel 1-substituted 1H-imidazo-[4,5-c]quinolin-4-amines are disclosed. These compounds function as antiviral agents, and they are potential synthetic intermediates in the preparation of known antiviral agents and labeled known antiviral agents. This invention also provides intermediates for preparing such compounds, pharmaceutical compositions containing such compounds, and pharmacological methods of using such compounds.

1 Claim, No Drawings

OLEFINIC 1H-IMIDAZO[4,5-C]QUINOLIN-4-AMINES

CROSS REFERENCE TO RELATED APPLICATION

This application is a continuation-in-part of U.S. Ser. No. 07/327,693, filed on March 23, 1989 now U.S. Pat. No. 4,929,624.

BACKGROUND OF THE INVENTION

1. Field of the Invention

This invention pertains to 1H-imidazo[4,5-c]quinoline compounds. More particularly, this invention pertains to antiviral 1H-imidazo[4,5-c]quinolin-4-amine compounds, intermediates for the preparation of such compounds, pharmaceutical compositions containing such compounds, and pharmacological methods of using such compounds.

2. Description of the Related Art

The first reliable report of the 1H-imidazo[4,5-c]quinoline ring system, Backman et al., J. Org. Chem. 15, 1278–1284 (1950), describes the synthesis of 1-(6-methoxy-8-quinolinyl)-2-methyl-1H-imidazo[4,5-c]-quinoline for possible use as an antimalarial agent. Subsequently, syntheses of various substituted 1H-imidazo[4,5-c]quinolines have been reported. For example, Jain et al., J. Med. Chem. 11, pp. 87–92 (1968), has synthesized the compound 1-[2-(4-piperidyl)ethyl]-1H-imidazo[4,5-c]quinoline as a possible anticonvulsant and cardiovascular agent. Also, Baranov et al., Chem. Abs. 85, 94362 (1976), has reported several 2-oxoimidazo[4,5-c]quinolines, and Berenyi et al., J. Heterocyclic Chem. 18, 1537–1540 (1981), has reported certain 2-oxoimidazo[4,5-c]quinolines.

Certain 1H-imidazo[4,5-c]quinolin-4-amines are described in U.S. Pat. No. 4,689,338. These compounds are substituted on the 1-position by alkyl, hydroxyalkyl, acyloxyalkyl, benzyl, phenylethyl or substituted phenylethyl, and are useful as antiviral agents. Furthermore, these compounds are known to induce interferon biosynthesis.

DETAILED DESCRIPTION OF THE INVENTION

This invention provides compounds of Formula I

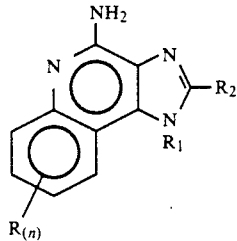

wherein $R_1$ is selected from the group consisting of straight chain or branched chain alkenyl containing 2 to about 10 carbon atoms and substituted straight chain or branched chain alkenyl containing 2 to about 10 carbon atoms, wherein the substituent is selected from the group consisting of straight chain or branched chain alkyl containing 1 to about 4 carbon atoms, cycloalkyl containing 3 to about 6 carbon atoms and cycloalkyl containing 3 to about 6 carbon atoms substituted by straight chain or branched chain alkyl containing 1 to about 4 carbon atoms; and $R_2$ is selected from the group consisting of hydrogen, straight chain or branched chain alkyl containing one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl containing one to about four carbon atoms, straight chain or branched chain alkoxy containing one to about four carbon atoms, and halogen, with the proviso that when the benzene ring is substituted by two such moieties, then the moieties together contain no more than 6 carbon atoms; and each R is independently selected from the group consisting of straight chain or branched chain alkoxy containing one to about four carbon atoms, halogen, and straight chain or branched chain alkyl containing one to about four carbon atoms, and n is an integer from zero to 2, with the proviso that if n is 2, then said R groups together contain no more than 6 carbon atoms; or a pharmaceutically acceptable acid addition salt thereof. Compounds of Formula I are useful as antiviral agents.

For the purposes of the instant specification and claims, the term "lower" when used in conjunction with "alkyl" or "alkoxy" designates straight chain or branched chain substituents containing 1 to about 4 carbon atoms.

$R_1$ preferably contains two to about ten carbon atoms. More preferably $R_1$ contains two to about eight carbon atoms. Most preferably, $R_1$ is ethenyl, 1-propenyl, 2-propenyl, or ethenyl or 2-propenyl substituted by lower alkyl.

$R_2$ is preferably benzyl, phenylethyl, lower alkyl, or hydrogen, most preferably lower alkyl or hydrogen.

Other substituents that contain an alkyl radical (e.g., R when R is alkoxy or alkyl, or lower alkyl or lower alkoxy substituents on $R_1$) preferably contain two carbon atoms or, more preferably, one carbon atom in each alkyl radical.

The halogen substituents are selected from fluorine, chlorine and bromine. Preferred halogen substituents are fluorine and chlorine.

It is preferred that n of Formula I be zero or one. It is most preferred that n of Formula I be zero.

Preferred compounds are: 1-(2-methyl-2-propenyl)-1H-imidazo[4,5-c]quinolin-4-amine: 1-(2-methyl-1-propenyl)-1H-imidazo[4,5-c]quinolin-4-amine, and 1-(2-propenyl)-1H-imidazo[4,5-c]quinolin-4-amine.

A compound of the invention of Formula I can be prepared as described in Scheme I below, wherein R, $R_1$, $R_2$ and n are as defined above and $R_{OH}$ is a latent $R_1$ substituent, e.g., hydroxyalkyl or like substituent comprising a leaving group susceptible to removal by an elimination, dehydration, or like reaction well known to those skilled in the art, to afford a substituent $R_1$ as described above. Such $R_{OH}$ substituents include 2-hydroxyethyl, 2-hydroxy-2-methylpropyl, 2-hydroxy-1-methylethyl, 2,2-dimethyl-2-hydroxypropyl, and the like. Tertiary hydroxy groups are preferred, because they are more susceptible to removal.

Many quinolines of Formula III are known compounds (see, for example, U.S. Pat. No. 3,700,674 and references cited therein). Those that are not known can be prepared by known methods, for example, from 4-hydroxy-3-nitroquinolines as illustrated in step (1) of Scheme I. Step (1) can be conducted by reacting the 4-hydroxy-3-nitroquinoline of Formula II with phosphorus oxychloride. The reaction is preferably conducted in N,N-dimethylformamide and is preferably accompanied by heating. Preferably, a large molar excess of phosphorus oxychloride is avoided. Use of about 1-2 moles of phosphorus oxychloride per mole of the 4-hydroxy-3-nitroquinoline of Formula II has been found to be particularly preferable.

In step (2) a 3-nitro-4-chloroquinoline of Formula III is reacted by heating with an aminoalcohol of the formula $R_{OH}NH_2$, wherein $R_{OH}$ is as defined above, in a suitable solvent such as water, dichloromethane, or tetrahydrofuran, to provide a quinoline of Formula IV. Some of the compounds of Formula IV are novel.

branched chain alkyl group containing 1 to about 4 carbon atoms, or (iv) a combination of such a carboxylic acid with such a trialkyl ortho ester to provide a compound of Formula VI. The reaction can be carried out by heating, e.g., at about 130° C., in the presence of an acid, preferably a carboxylic acid of the formula $R_2CO_2H$. Some of the compounds of Formula VI are novel.

Step (5) provides an intermediate of Formula VII, through oxidation of a compound of Formula VI with a conventional oxidizing agent that is capable of forming N-oxides but does not oxidize a hydroxyl group on $R_{OH}$ if one is present. If, however, $R_{OH}$ is not capable of oxidation, a wider range of conventional oxidizing agents is useful. Preferred oxidizing agents include

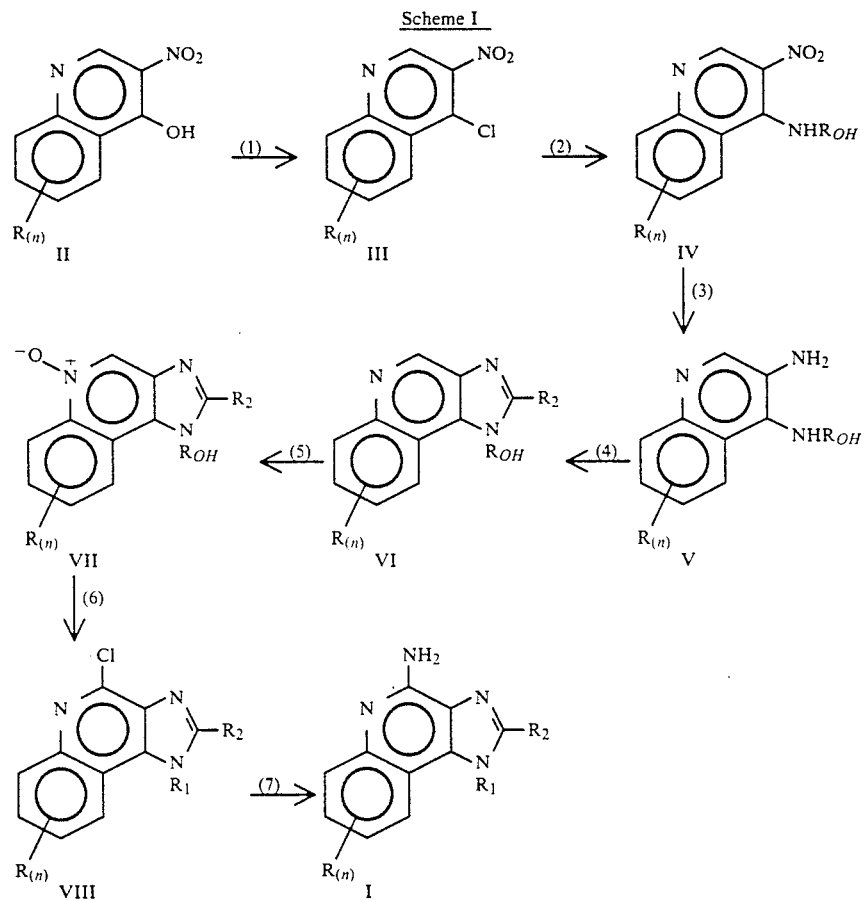

Scheme I

Steps (1) and (2) can be combined such that the 3-nitro-4-chloroquinoline need not be isolated prior to reaction with the compound of the formula $R_{OH}NH_2$. Such a reaction is exemplified in Example 134 and Example 188 (Step A) of U.S. Pat. No. 4,689,338, the disclosure of which is incorporated herein by reference.

A compound of Formula IV is reduced in step (3) preferably using a catalyst such as platinum on charcoal, to provide a compound of Formula V. The reduction can be carried out conveniently on a Paar apparatus in an inert solvent such as toluene or a lower alkanol. Some compounds of Formula V are novel.

In step (4) an intermediate compound of Formula V is reacted with (i) a 1,1-dialkoxyalkyl alkanoate such as diethoxymethyl acetate, or (ii) a carboxylic acid of the formula $R_2CO_2H$, which will introduce the desired $R_2$ group, or (iii) a trialkyl ortho ester of the formula $R_2C(Oalkyl)_3$, wherein "alkyl" is a straight chain or peroxyacids and hydrogen peroxide. The oxidation reaction is preferably conducted in glacial acetic acid. Heating is generally employed to accelerate the rate of reaction.

It is sometimes useful to protect a hydroxy group, with, for example, an alkanoyloxy group such as acetoxy or with benzoyloxy, for step(s) (5) and/or (6) and/or (7), and then to remove the protecting group and eliminate to form the compound of Formula I. Such protecting groups and reactions for their placement and removal are well known to those skilled in the art. See, for example, U.S. Pat. 4,689,338, Examples 115 to 123.

Step (6) as illustrated is a step particularly amenable to compounds of Formula VII wherein $R_{OH}$ is a hydroxyalkyl group in which the hydroxyl group is capable of elimination to form an $R_1$ substituent. In step (6)

an N-oxide of Formula VII is heated in the presence of a suitable chlorinating agent such as phosphorus oxychloride to provide an intermediate of Formula VIII. Two reactions occur: (1) the N-oxide is removed with concomitant chlorination of the 4-position, and (2) the hydroxyl group is eliminated to form the olefinic double bond of $R_1$. In practice, this elimination has occurred without external heating and in various solvents, particularly in larger scale reactions. This is thought to be a result of localized overheating. The best synthetic results are obtained by refluxing a compound of Formula VII in neat phosphorus oxychloride. Alternatives to step (6) that are useful for compounds of Formula VII wherein $R_{OH}$ comprises a leaving group other than hydroxyl include, for example, first eliminating the leaving group to form the olefinic double bond of $R_1$, and subjecting the resulting compound to the chlorination conditions recited above in connection with step (6) to form a compound of Formula VIII.

In step (7) the 4-chloro group is replaced by a 4-amino group to provide a compound of Formula I. The reaction is carried out in the presence of ammonium hydroxide or, preferably, ammonia. Preferably the intermediate of Formula VIII is heated at 125° to 175° C. under pressure for 6–24 hours. Preferably the reaction is conducted in a sealed reactor in the presence of either ammonium hydroxide or a solution of ammonia in an alkanol, (e.g., preferably about 15% ammonia in methanol).

Some compounds of Formula I can be prepared via 1H-imidazo[4,5-c]quinolin-4-amines of Formula XVI as described in Schemes II and III below, wherein R, $R_2$ and n are as defined above and $R_1'$ is a substituent capable of being subjected to an elimination or like reaction to afford a 1H-imidazo[4,5-c]quinolin-4-amine. $R_1'$ can be any substituent that can be removed. Examples of general classes of $R_1'$ include groups that will yield a stable cation upon treatment with aqueous acid (e.g. tertiary substituents, meaning for the purposes of the instant specification and claims any substituent wherein the carbon atom bonded to the 1-nitrogen is fully substituted with electron-donating groups (for example hydroxy, alkoxy, acyloxy, halogen, alkyl, phenyl, and the like) and substituents from which the 1H-imidazo[4,5-c]quinolin-4-amine can be eliminated (e.g. 2-hydroxyalkyl groups). Such $R_1'$ substituents include 1,1-dimethylethyl (i.e., t-butyl), 1,1-dimethyl-2-hydroxyethyl, 2-hydroxy-1-phenyl-1-methylethyl, 1,1-dimethyl-2-hydroxypropyl, and the like.

In step (1) of Scheme II a 3-nitro-4-chloroquinoline of Formula III is reacted by heating with an aminoalcohol of the formula $R_1'NH_2$, wherein $R_1'$ is as defined above, in a suitable solvent such as dichloromethane, water, or tetrahydrofuran, to provide a quinoline of Formula X.

Steps (2) and (3) can be combined such that the 3-nitro-4-chloroquinoline need not be isolated prior to reaction with $R_1'NH_2$, Such a reaction is exemplified Scheme II

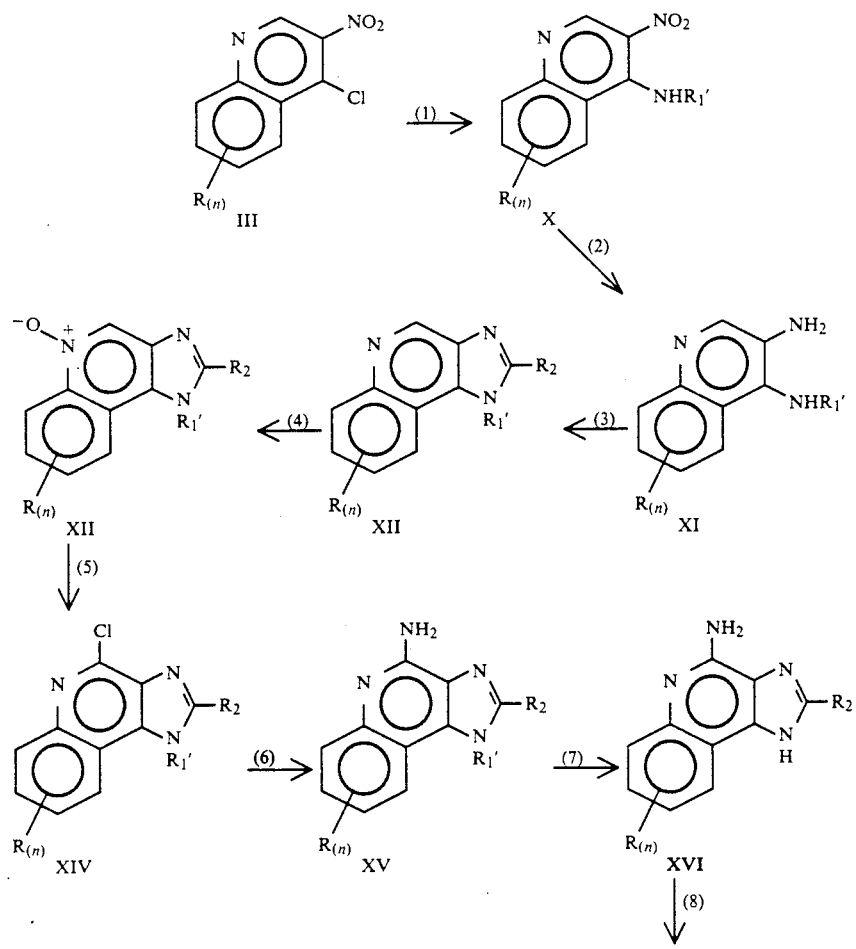

Scheme II
-continued

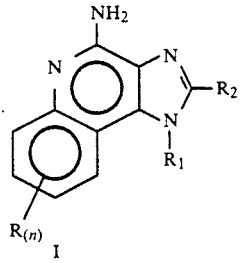

I in Example 134 and Example 188 (Step A) of U.S. Pat. No. 4,689,338, the disclosure of which is incorporated herein by reference.

A compound of Formula X is reduced in step (2) preferably using a catalyst such as platinum on charcoal, to provide a compound of Formula XI. The reduction can be carried out conveniently on a Paar apparatus in an inert solvent such as toluene or a lower alkanol.

In step (3) an intermediate compound of Formula XI is reacted with (i) a 1,1-dialkoxyalkyl alkanoate such as diethoxymethyl acetate, or (ii) a carboxylic acid that will introduce the desired $R_2$ group, or (iii) a trialkyl ortho ester of the formula $R_2C(Oalkyl)_3$, wherein "alkyl" is an alkyl group containing 1 to about 4 carbon atoms, or (iv) a combination of such a carboxylic acid with such a trialkyl ortho ester to provide a compound of Formula XII. The reaction can be carried out by heating, e.g., at about 130° C., in the presence of an acid, preferably an alkanoic acid having one more carbon atoms than $R_2$.

Step (4) provides an intermediate of Formula XIII. First, the hydroxy group, if one is present in $R_1'$, is protected with, for example, an alkanoyloxy group such as acetoxy, or with benzoyloxy. Such protecting groups and reactions for their placement and removal are well known to those skilled in the art. See, for example, U.S. Pat. No. 4,689,338, Examples 115 to 123. The resulting protected compound is then oxidized with a conventional oxidizing agent that is capable of forming N-oxides. Preferred oxidizing agents include peroxyacids and hydrogen peroxide. The oxidation reaction is preferably conducted in glacial acetic acid. Heating is generally employed to accelerate the rate of reaction.

In step (5) an N-oxide of Formula XIII is first heated in the presence of a suitably chlorinating agent such as phosphorus oxychloride to provide an intermediate of Formula XIV. It is preferred that phosphorus oxychloride be used in combination with a solvent (e.g., dichloromethane) inert to conventional chlorinating agents. It is also possible to run the reaction in the presence of a catalytic amount of N,N-dimethylformamide. The second part of step (5) involves removal of the protecting group, if one is present, by methods well known to those skilled in the art. When the protecting group is acetyl, hydrolysis with ammonia in methanol is preferred.

In step (6) the 4-chloro group is replaced by a 4-amino group to provide a compound of Formula XV. The reaction is carried out in the presence of ammonium hydroxide or, preferably, ammonia. Preferably the intermediate of Formula XIV is heated at 125° to 175° C. under pressure for 6-24 hours. Preferably the reaction is conducted in a sealed reactor in the presence of either ammonium hydroxide or a solution of ammonia in an alkanol, (e.g., 15% ammonia in methanol).

In step (7), a compound of Formula XV is heated in the presence of aqueous acid to effect the deamination of the $R_1'$ group, thus providing a 1H-imidazo[4,5-c]quinolin-4-amine of Formula XVI. Preferred conditions for the reaction include brief (e.g., 30 minute) reflux in dilute (e.g. 4N) aqueous hydrochloric acid.

Two alternate routes for the preparation of a compound of Formula XVI are shown in Scheme III, wherein R, $R_1'$, $R_2$ and n are as defined above. In step (1) of Scheme III, a compound of Formula XIII (prepared as set forth above in connection with Scheme II) is reacted with a reagent such as acetic anhydride and undergoes a rearrangement reaction to afford a 4-hydroxy compound of Formula XX. Other suitable reagents for the conversion include tosyl chloride, or various acyl halides such as acetyl chloride, in the presence of hydroxide (e.g. potassium hydroxide, sodium hydroxide, calcium hydroxide, and the like). Also, the transformation can be carried out by reaction with boron trifluoride followed by heating with phosphoric acid.

Step (2) of Scheme III illustrates the transformation of a compound of Formula XX to a compound of Formula XXI by first removing the protecting group, if one is present, from the 1-substituent. For example, if $R_1'$ contains a hydroxy group, this group will have been acylated in the previous step. $R_1'$ is then removed by heating with dilute aqueous acid (e.g., 4N to 6N acid) as described above in connection with step (7) of Scheme II. A compound of Formula XXI can then be converted as illustrated in steps (3) and (4) to a compound of Formula XVI.

A second alternative route shown in Scheme III for preparing a compound of Formula XVI begins with a compound of Formula XXII, some of which have been reported in East German Patent 242,806-A1, the disclosure of which is incorporated herein by reference. As shown in step (5) of Scheme III, a compound of Formula XXII can be reacted as described above in connection with step (3) of Scheme II to provide a compound of Formula XXI. A compound of Formula XXI, in turn, can be converted, also as discussed above, to a compound of Formula XVI.

In step (8) of Scheme II and step (5) of Scheme III, a compound of Formula I is prepared by alkylation of the 1-position of a compound of Formula XVI with an appropriate alkylating agent of the formula $R_1$-X, wherein X is a leaving group capable of being displaced by the nitrogen at the 1-position of a compound of Formula XVI.

The compounds of the invention can be readily reduced by methods well known to those skilled in the Scheme III

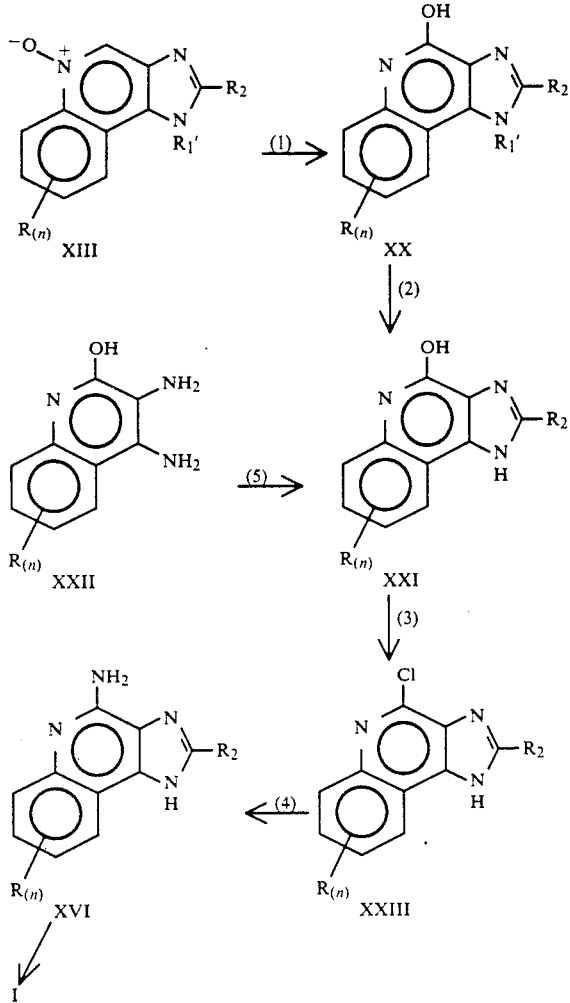

art to provide known antiviral agents substituted at the 1-position with alkyl, disclosed in U.S. Pat. No. 4,689,338. Also, should it be desired for the purposes of metabolic studies to prepare such a known antiviral agent with a label, e.g., a radiolabel such as tritium, on the alkyl group, the olefinic double bond of $R_1$ provides ready functionality for use in preparing such a labeled compound.

A compound of Formula I can be used as an antiviral agent itself or it can be used in the form of a pharmaceutically acceptable acid-addition salt such as a hydrochloride, dihydrogen sulfate, trihydrogen phosphate, hydrogen nitrate, methane sulfonate or a salt of another pharmaceutically acceptable acid. A pharmaceutically acceptable acid-addition salt of a compound of Formula I can be prepared, generally by reaction of the compound with an equimolar amount of a relatively strong acid, preferably an inorganic acid such as hydrochloric, sulfuric, or phosphoric acid, or an organic acid such as methanesulfonic acid, in a polar solvent. Isolation of the salt is facilitated by the addition of a solvent, such as diethyl ether, in which the salt is insoluble.

A compound of the invention can be formulated for the various routes of administration in a pharmaceutically acceptable vehicle, such as water or polyethylene glycol, along with suitable adjuvants, excipients, and the like. Particular formulations will be easily selected by those skilled in the art. Suitable formulations for topical application include creams, ointments and like formulations known to those skilled in the art, and generally contain less than 10% by weight of a compound of Formula I, preferably about 0.1% to 5% by weight of a compound of Formula I.

The compounds of the invention exhibit antiviral activity in mammals and can therefore be used to control viral infections. A preferred use of a compound of the invention is as an agent to control infections in mammals caused by Type I or Type II Herpes simplex virus. Generally, treatment is effective when a compound of Formula I or a formulation thereof is administered topically (e.g., intravaginally or on the skin), to a herpes infection. Compounds of Formula I can also be used to treat a herpes infection by oral or intraperitoneal administration.

The anti-Herpes activity of the compounds of Formula I relative to primary lesions caused by Type I or Type II Herpes simplex virus was demonstrated using the method described generally by Kern, et al., Antimicrob. Agents Chemother. 14, 817–823 (1978).

This method uses female guinea pigs of 200 to 300 grams in weight, preferably 200 to 260 grams in weight. Hartley guinea pigs are the preferred strain. The guinea pigs are anesthetized with pentobarbital or methoxyflurane, and then infected intravaginally, using a cotton swab, with about $10^5$ plaque forming units of Herpes simplex virus, either type I or type II. A compound of Formula I is formulated preferably in saline or water using a surfactant such as "Tween 80" (a polyoxyethylene sorbitan monooleate, commercially available from Emulsion Engineering Inc., Elk Grove Village, Ill.). Alternatively, a compound of Formula I can be formulated in "PEG 400" (a polyethyleneglycol of average molecular weight of about 400, commercially available from Union Carbide Corporation), or in polyethyleneglycol cream. Application of the formulation is initiated at the predetermined interval after infection such as one hour after infection. The formulation is applied intravaginally, for example, twice daily for a predetermined number of days, typically five or seven days. Virus replication can be monitored by determining the amount of virus recovered with vaginal swabs taken, for example, on days 1, 2, 3, 5 or 7 after infection. Virus is eluted from the swab in 1 mL of cell growth medium (Medium 199, Gibco Laboratories, Grand Island, N.Y.) and virus titer is determined using cell monolayers. External lesions are scored daily for 10 days using the following scale: zero, no lesions; 1, redness or swelling; 2, a few small vesicles; 3, several large vesicles; 4, large ulcers and necrosis; 5, paralysis. The degree of inhibition of lesion development is determined by comparing lesion development in infected and untreated control animals to lesion development in infected and drug-treated animals. Comparison studies with known drugs such as phosphonacetic acid and acyclovir can also be conducted. The compounds of the invention reduce the number of lesions and the severity thereof.

We believe that the antiviral activity of the compounds of the invention is attributable to induction of interferon biosynthesis. Some of the compounds of Formula I induce the biosynthesis of interferon in human blood cells in culture. The compounds 1-(2-methyl-2-propenyl)-1H-imidazo[4,5-c]-quinolin-4-amine, 1-(2-methyl-1-propenyl)-1H-imidazo[4,5-c] quinolin-4-amine, and 1-(2-propenyl)-1H-imidazo[4,5-c]quinolin-4-amine, for example, induce the biosynthesis of interferon when tested according to the method set forth below.

INTERFERON INDUCTION IN HUMAN BLOOD CELLS IN CULTURE

This method is based on an assay described by H. Kirchner, Ch. Kleinicke and W. Digel in "A Whole-Blood Technique for Testing Production of Human Interferons by Leukocytes", Journal of Immunological Methods, 48: 213–219, 1982, incorporated herein by reference.

Activity is based on the measurement of interferon secreted into a culture medium. Interferon is measured by bioassay.

Whole blood is collected by venipuncture into EDTA ($K_3$) vacutainer tubes. Blood is diluted 1:10 with RPMI 1640 medium supplemented with 25 mM HEPES (N-2-hydroxyethylpiperazine-N'-2-ethansulfonic acid) and L-glutamine with 1% penicillin-streptomycin solution added (available from GIBCO, Grand Island, N.Y.). 200 µL portions of diluted blood are added to 96 well (flat bottom) MicroTest ™ II tissue culture plates (available from Falcon Plastics, Oxnard, Calif.).

Test compounds are solubilized in ethanol or DMSO then diluted with distilled water, 0.01N sodium hydroxide, or 0.01N hydrochloric acid. The choice of solvent will depend on the chemical characteristics of the compound being tested. It is preferred that the final concentration of either ethanol or DMSO does not exceed 1%. A compound is initially tested at concentrations of 0.5, 2.5 and 5.0 µg/mL. The assay is repeated using higher concentrations if necessary.

The solution of test compound is added in a volume (less than or equal to 50 µL) to the wells containing 200 µL of diluted whole blood. Solvent and/or medium is added to control wells (wells with no test compound) and as needed to adjust the final volume of each well to 250 µL. The plates are covered with plastic lids, vortexed gently and then incubated for 48 hours at 37° C. with a 5% carbon dioxide atmosphere.

Following incubation, the plates are covered with parafilm and then centrifuged at 1000 rpm for 15 minutes at 4° C. in a Damon IEC Model CRU-5000 centrifuge. Medium (about 150 µL) is removed from 4 to 8 wells and is pooled into 2 mL sterile freezing vials. Samples are maintained at −70° C. until analysis.

Samples are shipped on dry ice to Lee Biomolecular Research Laboratories, Inc., San Diego, Calif. Interferon is determined by bioassay, A549 human lung carcinoma cells challenged with encephalomyocarditis. The details of the bioassay method used by Lee Biomolecular have been described by G. L. Brennan and L. H. Kronenberg in "Automated Bioassay of Interferons in Micro-test Plates", BioTechniques, June/July, 78, 1989, incorporated herein by reference. Interferon dilutions and A549 cells are incubated at 37° C. for 12 to 24 hours. The incubated cells are infected with an inoculum of encephalomyocarditis. The infected cells are incubated for an additional period at 37° C. before quantifying the viral cytopathic effect. The viral cytopathic effect is quantified by staining followed by spectrophotometric absorbance measurements. The interferon assay can be either a type I assay in which cells are seeded in 96 well plates and grown to "confluence" prior to exposure to interferon dilutions, or a type II assay in which cells are seeded directly into wells containing interferon dilutions. Results are expressed as alpha reference units/mL based on the value obtained for NIH HU IF-L standard.

That biosynthesis of interferon is induced suggests that at least certain compounds of the invention might be useful in treating other diseases such as rheumatoid arthritis, warts, eczema, Hepatitis B, psoriasis, multiple sclerosis, essential thrombocythaemia, cancer such as basal cell carcinoma, and other neoplastic diseases.

The following examples are provided to illustrate the invention and are not intended to be limiting thereof.

EXAMPLE 1

Preparation of a Compound of Formula IV

To a stirred solution of 150 mL of dichloromethane, 10 mL of triethylamine and 6.7 g (0.075 mole) of 1-amino-2-methyl-2-propanol was added 10.4 g (0.05 mole) of 4-chloro-3-nitroquinoline. The solution was heated on a steam bath for about one hour then evaporated to remove the solvent. The residue was dissolved in dilute hydrochloric acid and filtered. The filtrate was made basic with concentrated ammonium hydroxide to reprecipitate the product. The product was separated by filtration and recrystallized twice from ethanol to provide the novel yellow solid 2-methyl-1-[(3-nitro-4-quinolinyl)amino]-2-propanol, m.p. 244°–246° C. (dec.). Analysis: Calculated for $C_{13}H_{15}N_3O_3$: %C, 59.8; %H, 5.8; %N, 16.0; Found: %C, 59.8; %H, 5.9; %N 16.1.

EXAMPLE 2

Using the method of Example 1, 4-chloro-3-nitroquinoline was reacted with 2-amino-2-methyl-1-propanol to afford 2-[(3-nitro-4-quinolinyl)amino]-1-propanol, m.p. 207°–211° C. Analysis: Calculated for $C_{12}H_{13}N_3O_3$: %C, 58.3; %H, 5.3; %N,17; Found: %C, 58.6; %H, 5.3; %N, 17.2.

EXAMPLE 3

Preparation of a Compound of Formula V

To a solution of 7.0 g (0.027 mole) of 2-methyl-1-[(3-nitro-4-quinolinyl)amino]-2-propanol (from Example 1) in 150 mL of ethanol and 200 mL of toluene was added about 1 g of 5% platinum on charcoal, and the mixture was hydrogenated on a Paar apparatus until no further reaction occurred. Filtration followed by evaporation in vacuo provided a residue which gradually solidified to yellow solid 2-methyl-1-[(3-amino-4-quinolinyl)amino]-2-propanol.

EXAMPLE 4

Preparation of a Compound of Formula V

A mixture of 27.9 g (0.113 mole) of 2-[(3-nitro-4-quinolinyl)amino]-1-propanol in 1.2 1 of ethyl acetate, 28 g of magnesium sulfate and 2.0 g of 5% platinum on charcoal was hydrogenated on a Paar apparatus until hydrogen uptake was completed. The catalyst and solid residue were removed by filtration and the filtrate was concentrated by evaporation to provide 2-[(3-amino-4-quinolinyl)amino]-1-propanol as a yellow oil.

EXAMPLE 5

Preparation of a Compound of Formula VI

2-Methyl-1-[(3-amino-4-quinolinyl)amino]-2propanol, (0.027 mole), a crude reaction product obtained by the method of Example 3 was mixed with 5 drops of 98% formic acid and 50 mL of triethyl orthoformate, and the resulting mixture was heated at 135°–140° C. for one hour. Evaporation provided a residue which was dissolved in dilute hydrochloric acid. The solution was basified with concentrated sodium hydroxide. The solid was separated by filtration and washed with water to provide alpha, alpha-dimethyl-1H-imidazo[4,5-c]quinoline-1-ethanol. When a sample of this product was recrystallized from ethyl acetate it had a melting point of 169°–170° C. Analysis: Calculated for $C_{14}H_{15}N_3O \cdot H_2O$: %C, 64.8; %H, 6.6; %N, 16.2; Found: %C, 65.1; %H, 6.6; %N, 16.4.

EXAMPLE 6

Alternative Preparation of a Compound of Formula VI

2-[(3-Amino-4-quinolinyl)amino]-1-propanol (0.113 mole) as a crude reaction product obtained by the method of Example 4, was mixed with a 20 percent molar excess of diethoxymethyl acetate (22.3g, 0.136 mole) and heated for 0.75 hour. To the mixture was added 150 mL of water. The resulting mixture was made basic with concentrated ammonium hydroxide, and extracted first with ethyl acetate, then with chloroform. The extracts were combined, dried over magnesium sulfate, and evaporated, slurried in 1:1 chloroform/diethyl ether and separated by filtration to provide the solid product, beta-methyl-1H-imidazo[4,5-c]-quinoline-1-ethanol, m.p. 170°–174° C. after recrystallization from ethanol with treatment with decolorizing carbon. Analysis: Calculated for $C_{13}H_{13}N_3O$: %C, 68.7; %H, 5.8; %N, 18.5; Found: %C, 68.5; %H, 5.8; %N, 18.5.

EXAMPLE 7

Preparation of a Compound of Formula VII

To a solution of 24.1 g (0.10 mole) of alpha, alpha-dimethyl-1H-imidazo[4,5-c]quinoline-1-ethanol (from Example 5) in 250 mL of acetic acid was added 22.6 g (0.20 mole) of 30% hydrogen peroxide. The mixture was heated at 65°–70° C. for 6 hours and was then evaporated. The residue was dissolved in water and then basified with saturated sodium bicarbonate solution, and the product precipitated. The product was separated by filtration, washed with water and dried. The solid was slurried with acetone, filtered, washed with acetone and dried to provide alpha, alpha-dimethyl-1H-imidazo[4,5-c]quinoline-1-ethanol-5-oxide.

EXAMPLE 8

Acetylation and N-Oxidation of a Compound of Formula VI

A mixture of 13.1 g (0.058 mole) of beta-methyl-1H-imidazo[4,5-c]quinoline-1-ethanol and 35 mL of acetic anhydride was heated at about 100° C. for two hours. To this solution was added 350 mL of methanol and the solution was stirred for about 0.5 hour. The solution was evaporated in vacuo and the residue was added to a saturated sodium bicarbonate solution. The mixture was extracted with chloroform, the extracts were dried over magnesium sulfate and concentrated to a volume of about 150 mL. To this solution was added 15 g (0.07 mole) of meta-chloroperbenzoic acid. The mixture was stirred for one hour, then washed with chloroform, saturated sodium bicarbonate solution and water. The organic layer was then dried over magnesium sulfate and concentrated by evaporation in vacuo to provide 1-(2-acetoxy-1-methylethyl)-1H-imidazo[4,5-c]-quinolin5-oxide.

EXAMPLE 9

Preparation of a Compound of Formula I

A mixture of about 0.1 g of 4-chloro-alpha, alpha-dimethyl-1H-imidazo[4,5-c]quinoline-1-ethanol and about 5 mL of phosphorus oxychloride was heated at its reflux temperature for 30 minutes. The mixture was poured over ice, then extracted with ethyl acetate. The extracts were analyzed by thin layer chromatography and found to contain a mixture of two isomers: 4-chloro-1-(2-methyl-1-propenyl)-1H-imidazo[4,5-c]quinoline and 4-chloro-1-(2-methyl-2-propenyl)-1H-imidazo[4,5-c]quinoline.

The mixture of isomers was chromatographed and separated on silica gel (grade 60), eluting with 1:1:1 ethyl acetate-dichloromethane-hexane. The slower moving fraction was determined to be 4-chloro-1-(2-methyl-2-propenyl)-1H-imidazo[4,5-c]quinoline by proton magnetic resonance spectral analysis.

The product 4-chloro-1-(2-methyl-2-propenyl)-1H-imidazo[4,5-c]quinoline from above was reacted with 18% methanolic ammonia as described in Example 10 below to yield a solid. The solid was extracted with hot ethanol, leaving an insoluble residue. The extracts were concentrated to about 20% of their original volume to provide white solid product, 1-(2-methyl-2-propenyl)-1H-imidazo[4,5-c]quinolin-4-amine, m.p. 290°–294° C. Analysis: Calculated for $C_{14}H_{14}N_4$: %C, 70.6; %H, 5.9; %N, 23.5; Found: %C, 70.6; %H, 6.0; %N, 23.6.

Similarly, the isomer 4-chloro-1-(2-methyl-1-propenyl)-1H-imidazo[4,5-c]quinoline was reacted with 19% ammonia in methanol to provide 1-(2-methyl-1-propenyl)-1H-imidazo[4,5-c]quinolin-4-amine, m.p. 284°–289° C. after recrystallization from ethanol. Analysis: Calculated for $C_{14}H_{14}N_4$: %C, 70.6; %H, 5.9; %N, 23.5; Found: %C, 70.6; %H, 5.9; %N, 23.4.

EXAMPLE 10

Preparation of a Compound of Formula I

A mixture of 5.0 g (0.019 mole) of a mixture of 4-chloro-1-(2-methyl-2-propenyl)-1H-imidazo[4,5-c]quinoline and 4-chloro-1-(2-methyl-1-propenyl)-1H-imidazo[4,5-c]-quinoline and 50 mL of 15% ammonia in methanol was heated in a sealed reactor at 150° C. for 6 hours. The mixture was cooled to about 20° C., then with an ice bath. A solid was separated from the mixture by filtration, washed with methanol and dried. The solid was recrystallized from N,N-dimethylformamide, boiled in water and filtered hot, then recrystallized again from N,N-dimethylformamide. Proton magnetic resonance spectral analysis of the product indicated both isomers 1-(2-methyl-2-propenyl)-1H-imidazo-[4,5-c]quinolin-4-amine and 1-(2-methyl-1-propenyl)-1H-imidazo[4,5-c]-quinolin-4-amine were present. The presence of these two isomers was supported by a satisfactory elemental analysis. Calculated for $C_{14}H_{14}N_4$: %C, 70.6; %H, 5.9; %N, 23.5; Found: %C, 70.3; %H, 6.0; %N, 23.3.

EXAMPLE 11

A compound of Formula I could be combined with a catalyst such as platinum on charcoal in a suitable solvent such as ethanol and reduced with hydrogen in a Paar apparatus to provide a product according to Formula I wherein $R_1$ is alkyl.

EXAMPLE 12

Alternative Preparation of a Compound of Formula I

Step A

To a stirred mixture of 10.2 g (0.036 mole) of 1-(2-acetoxy-1-methylethyl)-1H-imidazo[4,5-c]quinolin-5-oxide (prepared according to the method of Example 8) in 100 mL of dichloromethane was added in portions, 4.2 mL, 6.9 g (0.45 mole) of phosphorus oxychloride. After 4 hours the mixture was evaporated in vacuo. The residue was added to a saturated sodium bicarbonate solution, and that solution was extracted with chloroform. The chloroform layer was washed with both saturated sodium bicarbonate solution and water, dried over magnesium sulfate and evaporated in vacuo to yield light brown solid 1-(2-acetoxy-1-methylethyl)-4-chloro-1H-imidazo[4,5-c]quinoline.

Step B

A portion of the solid from Step A (5.0 g) was added to 100 mL of 13% ammonia in methanol and 10 mL of ammonium hydroxide. The mixture was stirred for 60 hours and evaporated in vacuo. The residue was washed with saturated sodium bicarbonate solution and the solid residue was collected. The solid was washed with water and dried, then recrystallized from ethanol. The resulting solid was eluted through a silica gel column with ethyl acetate to provide deacetylated product, m.p. 173°–175° C. Analysis: Calculated for $C_{13}H_{12}N_3OCl$: %c, 59.7; %H, 4.6; %N, 16.1; Found: %C, 59.6; %H, 4.7; %N, 15.8.

Step C

A sample of 5.0 g of the deacetylated product from Step B was combined with 75 mL of a solution of 13% ammonia in methanol in a sealed reactor and heated at 150° C. for six hours. The mixture was cooled to about 20° C., then evaporated. The solid residue was washed by slurrying in a solution of saturated sodium bicarbonate, separated by filtration, and dried. The solid was then recrystallized from 200 mL of ethanol to yield 2.4 g of 4-amino-alpha-methyl-1H-imidazo[4,5-c]quinoline-1-ethanol, m.p. 216°–221° C. Analysis: Calculated for $C_{13}H_{14}N_4O$: %C, 64.4; %H, 5.8%; %0, 23.1%; Found: %C, 64.5; %H, 6.0; %O, 23.2.

The product from Step C could be converted to a compound of Formula I.

EXAMPLE 13

Preparation of a Compound of Formula X

To a stirred solution of 67.1 g (0.322 mole) of 4-chloro-3-nitroquinoline in 800 mL cf dichloromethane was added 54 mL (0.38 mole) of triethylamine and 96 mL (0.96 mole) of 2-amino-2-methyl-1-propanol. The mixture was heated at reflux for one hour, then stirred at about 20° C. for about 16 hours. The mixture was concentrated by evaporation in vacuo and the residue was slurried in 1.5 l of water. The product was separated by filtration and dried to provide solid 2,2-dimethyl-2-[(3-nitro-4quinolinyl)amino]ethanol. The structural assignment was confirmed by comparison of the nuclear magnetic resonance spectrum to that of a sample which was previously used for elemental analysis. Analysis of earlier sample: Calculated for $C_{13}H_{15}N_3O_2$: %C, 59.8; %H, 5.8; %N, 16.1; Found %C, 59.9; %H, 5.8; %N, 16.1.

EXAMPLE 14

Preparation of a Compound of Formula XI

To a solution of 35 g (0.134 mole) of 2,2-dimethyl-2-[(3-nitro-4-quinolinyl)amino]ethanol (from Example 13) in 1.2 l of ethyl acetate was added 35 g of magnesium sulfate and about 2 g of 5% platinum on charcoal, and the mixture was hydrogenated on a Parr apparatus until no further reaction occurred. Filtration followed by evaporation in vacuo provided a residue which was yellow solid 2-[(3-amino-4-quinolinyl)amino]-2,2-dimethylethanol.

EXAMPLE 15

Preparation of a Compound of Formula XII

A crude reaction product obtained by the method of Example 14 of 0.39 mole of 2-[(3-amino-4-quinolinyl)amino]-2,2-dimethylethanol was mixed with 77.2 mL of diethoxymethyl acetate, and the resulting mixture was heated on a steam bath for 0.75 hour. Evaporation provided a residue which was diluted with 500 mL of water. The solid was separated by filtration and washed with water to provide light yellow crystals of beta,beta-dimethyl-1H-imidazo[4,5-c]quinoline-1-ethanol. When a sample of this compound from another preparation was recrystallized from ethyl acetate it had a melting point of 211°–216° C. Analysis: Calculated for $C_{14}H_{15}N_3O$: %C, 69.7; %H, 6.3; %N, 17.4; Found: %C, 70.0; %H, 6.3; %N, 17.4.

EXAMPLE 16

Acetylation and N-Oxidation of a Compound of Formula XII

A mixture of 67.8 g (0.281 mole) of beta, beta-dimethyl-1H-imidazo[4,5-c]quinoline-1-ethanol and 170 mL of acetic anhydride was heated at about 100° C. for three hours. To this solution was added 1700 mL of methanol and the solution was refluxed for about 0.5 hour. The solution was evaporated in vacuo and the residue was basified with a saturated sodium bicarbonate solution. Scratching provided an off-white solid which was separated by filtration, washed with water and dissolved in chloroform. The solution was dried over magnesium sulfate and concentrated to a solid residue. The solid was dissolved in 750 mL of chloroform. To this solution was added 67.3 g (0.312 mole) of meta-chloroperbenzoic acid. The mixture was stirred for three hours, evaporated, then washed with saturated sodium bicarbonate solution. Sodium chloride was added, then the mixture was extracted with chloroform. The organic layer was then dried over magnesium sulfate and concentrated by evaporation in vacuo to provide 1-(2-acetoxy-1,1-dimethylethyl)-1H-imidazo[4,5-c]quinoline-5-oxide.

EXAMPLE 17

Preparation of a Compound of Formula XIV

Step A

To a stirred mixture of 76.6 g (0.256 mole) of 1-(2-acetoxy-1,1-dimethylethyl)-1H-imidazo[4,5-c]quinoline-5-oxide in 0.75 liters of dichloromethane was added in portions 43.2 g of phosphorus oxychloride. The reaction was exothermic. The reaction mixture was allowed to cool on standing and stirred for 4 hours. The mixture was evaporated in vacuo. The residue was neutralized with a saturated sodium bicarbonate solution, and that solution was filtered to separate the solid product. The product was dissolved in dichloromethane. The organic layer was washed with water, dried over magnesium sulfate and evaporated in vacuo. The light brown solid was assumed to be the expected 4-chloro compound, 1-(2-acetoxy-1,1-dimethylethyl)-4-chloro-1H-imidazo[4,5-c]quinoline.

Step B

The solid from Step A was added to 750 mL of 17% ammonia in methanol and 75 mL of ammonium hydroxide. After stirring for about 64 hours the mixture was evaporated in vacuo, the residue was slurried with saturated sodium bicarbonate solution and the solid residue was collected by filtration. The solid was washed with water and dried providing 4-chloro-beta,beta-dimethyl-1H-imidazo[4,5-c]quinoline-1-ethanol. The structural assignment was confirmed by nuclear magnetic resonance spectral analysis. When a sample of this compound from another run was recrystallized from ethanol it had a melting point of 207°–210° C. Analysis: Calculated for $C_{14}H_{14}N_3OCl$ %C, 61.0; %H, 5.1; %N, 15.2; Found: %C, 61.2; %H, 5.1; %N, 15.2.

EXAMPLE 18

Preparation of a Compound of Formula XV

A sample of 4.1 g of the deacetylated product from Step B of Example 17 was combined with 75 mL of a solution of 18% ammonia in methanol in a sealed reactor and heated at 150° C. for six hours. The mixture was cooled to about 20° C., then the crystalline product was separated by filtration. The solid product was washed by slurrying in a solution of saturated sodium bicarbonate, separated by filtration, washed with water and dried. The solid was recrystallized from methanol, treating with decolorizing charcoal, to provide colorless crystals of 4-amino-beta,beta-dimethyl-1H-imidazo[4,5-c]quinoline-1-ethanol, m.p. 277°–281° C. Analysis: Calculated for $C_{14}H_{16}N_4O$: %C, 65.5; %H, 6.3; %N, 21.9; Found: %C, 65.6; %H, 6.3; %N, 21.7.

EXAMPLE 19

Preparation of a Compound of Formula XII

A mixture of 26.7 g (0.115 mole) of 2-[(3-amino-4-quinolinyl)amino]-2,2-dimethyl-1-ethanol and 42.8 g (0.180 mole) of triethyl orthophenylacetate was heated at 130° C. for four hours. The mixture was diluted with water, acidified to pH 5 with 6N hydrochloric acid and diluted with diethyl ether. The solid which precipitated was separated by filtration, rinsed with diethyl ether and slurried in saturated sodium bicarbonate solution. The solid was separated by filtration and dried to provide beta,beta-dimethyl-2-phenylmethyl-1H-imidazo[4,5-c]quinoline-1-ethanol. The structural assignment was confirmed by nuclear magnetic resonance spectral analysis.

EXAMPLE 20

Preparation of a Compound of Formula XIII

Using the method described in Example 16, the product from Example 19, 2,2-dimethyl-(2-phenylmethyl-1H-imidazo[4,5-c]quinoline)-1-ethanol was acetylated to provide 1-(2-acetoxy-1,1-dimethylethyl)-2-phenylmethyl-1H-imidazo[4,5-c]quinoline which was oxidized to provide solid 1-(2-acetoxy-1,1-dimethylethyl)-2-phenylmethyl-1H-imidazo[4,5-c]quinoline-5-oxide.

EXAMPLE 21

Preparation of a Compound of Formula XIV

Using the method described in Example 17, Parts A and B, the product from Example 20, 1-(2-acetoxy-1,1-dimethylethyl)-2-phenylmethyl-1H-imidazo[4,5-c]quinoline-5-oxide was chlorinated to provide 4-chloro-1-(2-acetoxy-1,1-dimethylethyl)-2-phenylmethyl-1H-imidazo[4,5-c]quinoline which was deacetylated to provide 4-chloro-beta,beta-dimethyl-2-phenylmethyl-1H-imidazo[4,5-c]quinoline-1-ethanol. Recrystallization from ethyl acetate gave tan crystals, m.p. 262°–266° C. Analysis: Calculated for $C_{21}H_{20}N_3OCl$: %C, 68.9; %H, 5.5; %N, 11.5; Found: %C, 68.6; %H, 5.5; %N, 11.3.

EXAMPLE 22

Preparation of a Compound of Formula XVI

Step A

The method described in Example 18 except 13% ammonia in methanol was used to aminate 4-chloro-beta,beta-dimethyl-2-phenylmethyl-1H-imidazo[4,5-c]quinolin-1-ethanol from Example 21 to provide 2-(4-amino-2-phenylmethyl-1H-imidazo[4,5-c]quinoline)-2,2-dimethyl-1-ethanol.

Step B

To the 4-amino compound from Step A above was added 100 mL of 20% hydrochloric acid and the mixture was heated at reflux for three hours. The mixture was cooled to about 20° C., the solid precipitate was separated by filtration to provide 2-phenylmethyl-1H-imidazo[4,5-c]quinolin-4-amine hydrochloride.

Step C

The hydrochloride salt from Step B was slurried in saturated sodium bicarbonate solution. The free base was a solid and was separated by filtration and dried. Recrystallization from ethanol provided solid 2-phenylmethyl-1H-imidazo[4,5-c]quinolin-4-amine, m.p. 274°–277° C. Analysis: Calculated for $C_{17}H_{14}N_4$: %C, 74.4; %H, 5.1; %N, 20.4; Found: %C, 73.8; %H, 5.2; %N, 20.1.

EXAMPLE 23

Preparation of a Compound of Formula X

A solution of 19 g (0.10 mole) of 4-hydroxy-3-nitroquinoline, 200 mL of dichloromethane, 10 mL of N,N-dimethylformamide and 10 mL of phosphorus oxychloride was stirred at about 20° C. for 30 minutes and then heated at its reflux temperature for 30 minutes. The solution was cooled to about 20° C. and diluted with 300 mL of diethyl ether. This solution was stirred for 30 minutes at 20° C., treated with decolorizing charcoal and filtered through celite. The filtrate was washed repeatedly with 200 mL portions of cold sodium bicarbonate solution until foaming stopped and the washings were basic. The solution containing 4-chloro-3-nitroquinoline was dried over magnesium sulfate and filtered and evaporated in vacuo. To the solid was added a mixture of 20 g of tertiary-butylamine and 100 mL of N,N-dimethylformamide and the mixture was heated on a steam bath for about one hour. To this mixture was added about 200 mL of water and the product was isolated by filtration and recrystallized from hexane to provide N-(1,1-dimethylethyl)-3-nitro- 4-quinolinamine, m.p. 106°-108° C. Analysis: Calculated for $C_{13}H_{15}N_3O_2$: %C, 63.7; %H, 6.2; %N, 17.1; Found: %C, 64.0; %H, 6.3; %N, 17.1.

EXAMPLE 24

Preparation of a Compound of Formula XII

A mixture of 17.7 g (0.0722 mole) of N-(1,1-dimethylethyl)-3-nitro-4-quinolinamine, 350 mL of ethyl acetate, 20 g of magnesium sulfate and about one gram of platinum on charcoal was hydrogenated on a Paar apparatus. After hydrogen pressure stabilized, the mixture was filtered and the filtrate was evaporated to provide a solid residue of 3-amino-N-(1,1-dimethylethyl)-4-quinolinamine.

To the solid was added 20 mL (0.12 mole) of diethoxymethyl acetate and the solution was heated on a steam bath for one hour. The solution was cooled to about 20° C., diluted with water and basified with concentrated ammonium hydroxide. After standing for about 0.5 hour the mixture was extracted with diethyl ether, the extracts were dried over magnesium sulfate and the mixture was filtered. The filtrate was evaporated to dryness and the oily residue gradually solidified. The residue was slurried and washed in hexane, the product was separated by filtration and dried to provide light orange solid 1-(1,1-dimethylethyl)-1H-imidazo[4,5-c]quinoline, melting point after recrystallization from diethyl ether 145°-147° C. Analysis: Calculated for $C_{14}H_{15}N_3$: %C, 74.5; %H, 6.7; %N 18.7; Found: %C, 74.6; %H, 6.7; %N, 18.6.

EXAMPLE 25

Preparation of a Compound of Formula XIII

To a solution of 23.5 g (0.104 mole) of 1-(1,1-dimethylethyl)-1H-imidazo[4,5-c]quinoline in 200 mL of chloroform was added 23.4 g (0.115 mole) of meta-chloroperbenzoic acid. The mixture was stirred at about 20° C. for 24 hours. The solution was basified with saturated sodium bicarbonate solution, then dried over magnesium sulfate. Filtration of the mixture, followed by evaporation in vacuo provided a cream colored solid. The solid residue was slurried in dilute ammonium hydroxide, then filtered, washed with water and dried, to provide white solid 1-(1,1-dimethylethyl)-1H-imidazo[4,5-c]quinoline-5-oxide.

EXAMPLE 26

Preparation of a Compound of Formula XIV

Using the method of Example 17, Step A, 1-(1,1-dimethylethyl)-1H-imidazo[4,5-c]quinoline-5-oxide was chlorinated to provide 4-chloro-1-(1,1-dimethylethyl)-1H-imidazo[4,5-c]quinoline which was recrystallized from diethyl ether. Analysis: Calculated for $C_{14}H_{14}ClN_3$: %C, 64.7; %H, 5.4; %N, 16.2; Found: %C, 64.9; %H, 5.4; %N, 16.1.

EXAMPLE 27

Preparation of a Compound of Formula XV

Using the method of Example 22, Step A, 4-chloro-1-(1,1-dimethylethyl)-1H-imidazo[4,5-c]quinoline was aminated to provide 1-(1,1-dimethylethyl)-1H-imidazo[4,5-c]quinolin-4-amine. Recrystallization from a mixture of ethanol and dichloromethane provided colorless crystals, m.p. 275°-285° C. (dec). Analysis: Calculated for $C_{14}H_{16}N_4$: %C, 70.0; %H, 6.7; %N, 23.3; Found: %C, 70.1; %H, 6.8; %N, 23.4.

EXAMPLE 28

Preparation of a Compound of Formula XVI

A mixture of 1.5 g (0.0062 mole) of 1-(1,1-dimethylethyl)-1H-imidazo[4,5-c]quinolin-4-amine and 25 mL of 6N hydrochloric acid was heated at its reflux temperature for 30 minutes. The mixture was filtered hot and the precipitate was slurried in saturated sodium bicarbonate solution. The solid was again separated by filtration, washed with water and dried. Recrystallization from ethanol provided colorless (white) crystals of 1H-imidazo[4,5-c]quinolin-4-amine, m.p. greater than 300° C.

EXAMPLE 29

Preparation of a Compound of Formula XXI

A mixture of 1.5 g (0.086 mole) of known compound 2-hydroxy-3,4-quinolinediamine and 10 mL of diethoxymethyl acetate was heated at 125° C. for 0.5 hours. The mixture was diluted with 25 mL of water, then the mixture was basified with concentrated ammonium hydroxide. The product was separated by filtration, washed with water and ethanol and dried. Recrystallization from a mixture of water and N,N-dimethylformamide provided colorless solid 1H-imidazo[4,5-c]quinolin-4-ol. Analysis: Calculated for $C_{10}H_7N_3O$: %C, 64.9; %H, 3.8; %N, 22.7; Found: %C, 64.5; %H, 3.9; %N, 22.3.

EXAMPLE 30

Preparation of a Compound of Formula XXIII

A mixture of 500 mg of 1H-imidazo[4,5-c]quinolin-4-ol and about 6 mL of phosphorous oxychloride was heated on a steam bath for about 16 hours, then poured over ice. The mixture was neutralized with saturated sodium bicarbonate solution, then the solid was separated by filtration. The solid was dissolved in dilute hydrochloric acid, the mixture was filtered and the filtrate was neutralized with concentrated ammonium hydroxide to reprecipitate the product. Filtration and drying was followed by recrystallization from methanol to provide crystals of 4-chloro-1H-imidazo[4,5-c]quinoline. Analysis: Calculated for $C_{10}H_6N_3$: %C, 59.0; %H, 3.0; %N, 20.6; Found: %C, 59.5; %H, 3.0; %N, 20.2.

EXAMPLE 31

Alternate Preparation of a Compound of Formula XVI

Using the method of Example 18, the product of Example 30, 0.2g (0.0010 mole) of 4-chloro-1H-imidazo[4,5-c]quinoline was aminated at 175 ° C. in 12% ammonia in methanol to provide 1H-imidazo[4,5-c]quinolin-4-amine. The structure was verified by comparison of infrared and nuclear magnetic resonance spectra of the product with spectra of the product from Example 32 below.

EXAMPLE 32

Preparation of a Compound of Formula XVI

A stirred mixture of 5.6 g (0.022 mole of 4-amino-beta,beta-dimethyl-1H-imidazo4,5-c]quinoline1-ethanol and 150 mL of 20% hydrochloric acid was heated for one hour, cooled to about 20° C. and filtered to separate the solid product. The solid was slurried in aqueous ammonium hydroxide, filtered and dried. Recrystallization from ethanol with treatment with decolorizing charcoal provided white crystals of 1H-imidazo[4,5- c]quinolin-4-amine, m.p. greater than 300° C. The structural assignment was supported by infrared and nuclear magnetic resonance spectral analyses and comparison to the product from another preparation which had an analysis for $C_{10}H_8N_4$: %C, 65.2; %H, 4.4; %N, 30.4; Found: %C, 64.8; %H, 4.4; %N, 30.2.

EXAMPLE 33

Alternate Preparation of a Compound of Formula XXI

Step A

To a stirred mixture of 34.2 g (0.142 mole) of beta,-beta-dimethyl-1H-imidazo[4,5-c]quinolin-1-ethanol (from Example 15) in 200 mL of acetic acid was added 29 mL (0.284 mole) of 30% hydrogen peroxide and the mixture was heated at 65° C. for about 10 hours. The mixture was evaporated in vacuo, the residue was diluted with 200 mL of water and then basified with sodium bicarbonate solution. The precipitate was separated by filtration, washed with water and dried to provide light yellow solid 1-(2-hydroxy-1,1,-dimethyl)-1H-imidazo[4,5-c]quinoline-5-oxide.

Step B

A mixture of 28.8 g (0.112 mole) of 1-(2-hydroxy-1,1-dimethylethyl)-1H-imidazo[4,5-c]quinolin-5oxide and 100 mL of acetic anhydride was heated on a steam bath for 6 hours, cooled to about 20° C. and filtered. The solid which was obtained was rinsed with acetic anhydride, then diethyl ether to provide light gray solid 1-(2-acetoxy-1,1-dimethylethyl)-1H-imidazo[4,5-c]quinolin-4-ol. The structural assignment was supported by infrared and nuclear magnetic resonance spectral analyses.

Step C

A solution of 18.1 g (0.0605 mole) of 1-(2-acetoxy-1,1-dimethylethyl)-1H-imidazo[4,5-c]quinolin-4-ol and 500 mL of 6N hydrochloric acid was heated at its reflux temperature for one day and cooled to about 20° C. The solid salt, 1H-imidazo[4,5-c]quinolin-4-ol hydrochloride, was separated by filtration. The salt was neutralized by slurrying in saturated sodium bicarbonate solution. The solid was separated by filtration, dried, and further dried by twice repeated coevaporation with ethanol to provide tan solid 1H-imidazo[4,5-c]quinolin-4-ol. The structural assignment was supported by infrared and nuclear magnetic resonance spectral analyses and comparison with the spectra of the product from Example 29.

EXAMPLE 34

Alternate Preparation of a Compound of Formula XXIII

Step A

To 50 mL of acetic anhydride was added 11.5 g (0.0477 mole) of 1-(1,1-dimethylethyl)-1H-imidazo-[4,5-c]quinoline-5oxide (produce of Example 25) and the slurry was heated on a steam bath for a few minutes, then allowed to cool to about 20° C. The solid was separated by filtration and washed with an ethanol-hexane mixture. Slurrying with dilute ammonium hydroxide, filtration and washing with water provided solid which has recrystallized from an ethanol-dichloromethane mixture to provide colorless (white) crystals of 1-(1,1-dimethylethyl)-1H-imidazo[4,5-c]quinolin-4-ol, m.p. greater than 300° C. Analysis: Calculated for $C_{14}H_{15}N_3O$: %C, 69.7; %H, 6.3; %N, 17.4; Found: %C, 69.5; %H, 6.3; %N, 17.3.

Step B

A mixture of 13 g (0.054 mole) of 1-(1,1-dimethylethyl)-1H-imidazo[4,5-c]quinolin-4-ol and 100 mL of 6N hydrochloric acid was heated at reflux for about 30 minutes. The mixture was allowed to cool to about 20° C., then the solid was separated by filtration. The solid was slurried in dilute ammonium hydroxide, then separated by filtration, washed with water and dried. The solid was slurried in ethanol and heated on a steam bath to evaporate the ethanol. The white solid residue was 1H-imidazo[4,5-c]quinolin-4-ol.

Step C

To a mixture of 7.7 g (0.0416 mole) of 1H-imidazo[4,5-c]quinolin-4-ol and 50 mL of N,N-dimethylformamide was added in small portions 12 mL (0.13 mole) of phosphorus oxychloride. The mixture was heated on a steam bath for 1.5 hour, poured onto ice and basified with concentrated ammonium hydroxide. The solid precipitate was separated by filtration, washed with water and dried to provide 4-chloro-1H-imidazo[4,5-c]quinoline as a tan powder corresponding to the product of Example 30.

EXAMPLE 35

Preparation of a Compound of Formula I

To a stirred suspension of 2.0 g (0.011 mole) of 1H-imidazo[4,5-c]quinolin-4-amine in 20 mL of N,N-dimethylformamide was added to 0.36 g (0.012 mole) of 80% sodium hydride. This mixture was stirred for 40 minutes to give a clear solution. To this solution was added 1.48 g (0.012 mole) of allyl bromide. The resulting mixture was stirred at room temperature for about 1 hour then heated on a steam bath for about 1 hour. The reaction mixture was chilled in an ice bath and the precipitate collected by filtration. The precipitate was stirred with water, collected by filtration and dried to give 1.5 g of a solid. This solid was recrystallized from about 225 mL of ethanol to provide 1.27 g of 1-(2-propenyl)-1H-imidazo[4,5-c]quinolin-4-amine, m.p. 227°–280° C. The structural assignment was confirmed by nuclear magnetic resonance spectroscopy. Analysis: Calculated for $C_{13}H_{12}N_4$: %C, 69.6; %H, 5.4; %N, 25.0; Found: %C, 69.3; %H, 5.3; %N, 25.1.

We claim:

1. The compound 1-(2-propenyl)-1H-imidazo[4,5-c]quinolin-4-amine or a pharmaceutically acceptable addition salt thereof.

* * * * *